US 7,181,927 B2

(12) United States Patent
Collins et al.

(10) Patent No.: US 7,181,927 B2
(45) Date of Patent: Feb. 27, 2007

(54) PRIMARY HEAT EXCHANGER FOR PATIENT TEMPERATURE CONTROL

(75) Inventors: Kenneth A. Collins, Mission Viejo, CA (US); David Seari Kimball, Irvine, CA (US)

(73) Assignee: Alsius Corporation, Irvine, CA (US)

( * ) Notice: Subject to any disclaimer, the term of this patent is extended or adjusted under 35 U.S.C. 154(b) by 90 days.

(21) Appl. No.: 11/173,554

(22) Filed: Jul. 1, 2005

(65) Prior Publication Data

US 2007/0000278 A1    Jan. 4, 2007

(51) Int. Cl.
*F25D 17/02*    (2006.01)
*A61F 7/00*    (2006.01)

(52) U.S. Cl. .............. 62/434; 62/3.2; 607/104

(58) Field of Classification Search ............. 62/434, 62/3.2, 3.3; 165/104.18; 607/104, 106, 607/122
See application file for complete search history.

(56) References Cited

U.S. PATENT DOCUMENTS

| | | | |
|---|---|---|---|
| 4,309,592 A * | 1/1982 | Le Boeuf | 392/470 |
| 5,207,640 A | 5/1993 | Hattler | 604/28 |
| 5,230,862 A | 7/1993 | Berry et al. | 422/48 |
| 5,271,743 A | 12/1993 | Hattler | 604/26 |
| 5,450,516 A | 9/1995 | Pasquali et al. | 385/115 |
| 5,470,659 A | 11/1995 | Baumgart et al. | 428/398 |
| 5,725,949 A | 3/1998 | Pasquail et al. | 428/398 |
| 5,735,809 A | 4/1998 | Gorsuch | 428/364 |
| 5,755,690 A | 5/1998 | Saab | 604/96 |
| 5,837,003 A | 11/1998 | Ginsburg | 607/106 |
| 5,876,667 A | 3/1999 | Gremel et al. | 604/4 |
| 5,879,329 A | 3/1999 | Ginsburg | 604/93 |
| 5,989,238 A | 11/1999 | Ginsburg | 604/93 |
| 6,004,289 A | 12/1999 | Saab | 604/96 |
| 6,019,783 A | 2/2000 | Philips | 607/105 |
| 6,042,559 A | 3/2000 | Dobak | 604/7 |
| 6,096,068 A | 8/2000 | Dobak | 607/105 |
| 6,110,168 A | 8/2000 | Ginsburg | 606/27 |
| 6,126,684 A | 10/2000 | Gobin | 607/113 |
| 6,146,411 A | 11/2000 | Noda | 607/105 |
| 6,149,670 A | 11/2000 | Worthen | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak | 607/106 |
| 6,165,207 A | 12/2000 | Balding | 607/105 |
| 6,224,624 B1 | 5/2001 | Lasheras | 607/105 |
| 6,231,594 B1 | 5/2001 | Dae | 607/96 |
| 6,231,595 B1 | 5/2001 | Dobak | 607/106 |
| 6,235,048 B1 | 5/2001 | Dobak | 607/104 |
| 6,238,428 B1 | 5/2001 | Werneth | 607/105 |
| 6,245,095 B1 | 6/2001 | Dobak | 607/105 |

(Continued)

OTHER PUBLICATIONS

U.S. Appl. No. 60/272,442, Worthen et al.

*Primary Examiner*—Melvin Jones
(74) *Attorney, Agent, or Firm*—John L. Rogitz

(57) ABSTRACT

A system for exchanging heat with primary coolant flowing through an intravascular catheter or externally-applied pad to warm or cool a patient. A secondary heat transfer element can be engaged with a primary heat transfer element and is not grounded when the primary heat transfer element is fully engaged with the secondary heat transfer element during operation. In contrast, the secondary heat transfer element is grounded when the primary heat transfer element is at a predetermined disengaged position relative to the secondary heat transfer element.

17 Claims, 2 Drawing Sheets

U.S. PATENT DOCUMENTS

| | | | |
|---|---|---|---|
| 6,251,129 B1 | 6/2001 | Dobak | 607/105 |
| 6,251,130 B1 | 6/2001 | Dobak | 607/105 |
| 6,254,626 B1 | 7/2001 | Dobak | 607/105 |
| 6,264,679 B1 | 7/2001 | Keller | 607/105 |
| 6,287,326 B1 | 9/2001 | Pecor | 607/105 |
| 6,290,717 B1 | 9/2001 | Philips | 607/113 |
| 6,299,599 B1 | 10/2001 | Pham | 604/113 |
| 6,306,161 B1 | 10/2001 | Ginsburg | 607/106 |
| 6,312,452 B1 | 11/2001 | Dobak | 607/105 |
| 6,325,818 B1 | 12/2001 | Werneth | 607/105 |
| 6,338,727 B1 | 1/2002 | Noda | 604/113 |
| 6,364,899 B1 | 4/2002 | Dobak | 607/113 |
| 6,368,304 B1 | 4/2002 | Aliberto | 604/113 |
| 6,379,378 B1 | 4/2002 | Werneth | 607/96 |
| 6,383,210 B1 | 5/2002 | Magers | 607/105 |
| 6,393,320 B2 | 5/2002 | Lasersohn | 607/3 |
| 6,405,080 B1 | 6/2002 | Lasersohn | 607/3 |
| 6,409,747 B1 | 6/2002 | Gobin | 607/113 |
| 6,416,533 B1 | 7/2002 | Gobin | 607/113 |
| 6,419,643 B1 | 7/2002 | Shimada | 600/323 |
| 6,428,563 B1 | 8/2002 | Keller | 607/105 |
| 6,432,124 B1 | 8/2002 | Worthen | 607/105 |
| 6,436,130 B1 | 8/2002 | Philips | 607/105 |
| 6,436,131 B1 | 8/2002 | Ginsburg | 607/106 |
| 6,440,158 B1 | 8/2002 | Saab | 604/105 |
| 6,447,474 B1 | 9/2002 | Balding | 604/66 |
| 6,450,987 B1 | 9/2002 | Kramer | 604/523 |
| 6,450,990 B1 | 9/2002 | Walker | 604/113 |
| 6,451,045 B1 | 9/2002 | Walker | 607/105 |
| 6,454,792 B1 | 9/2002 | Noda | 607/105 |
| 6,454,793 B1 | 9/2002 | Evans | 607/105 |
| 6,458,150 B1 | 10/2002 | Evans | 607/105 |
| 6,460,544 B1 | 10/2002 | Worthen | 607/105 |
| 6,464,716 B1 | 10/2002 | Dobak | 607/105 |
| 6,468,296 B1 | 10/2002 | Dobak | 607/105 |
| 6,471,717 B1 | 10/2002 | Dobak | 607/105 |
| 6,475,231 B2 | 11/2002 | Dobak | 607/105 |
| 6,478,811 B1 | 11/2002 | Dobak | 607/105 |
| 6,478,812 B2 | 11/2002 | Dobak | 607/105 |
| 6,482,226 B1 | 11/2002 | Dobak | 607/104 |
| 6,491,039 B1 | 12/2002 | Dobak, III | 128/898 |
| 6,491,716 B2 | 12/2002 | Dobak | 607/105 |
| 6,494,903 B2 | 12/2002 | Pecor | 607/105 |
| 6,497,721 B2 | 12/2002 | Ginsburg | 607/106 |
| 6,516,224 B2 | 2/2003 | Lasersohn | 607/3 |
| 6,520,933 B1 | 2/2003 | Evans | 604/103.07 |
| 6,527,798 B2 | 3/2003 | Ginsburg | 607/106 |
| 6,529,775 B2 | 3/2003 | Whitebook | 607/100 |
| 6,530,946 B1 | 3/2003 | Noda | 607/113 |
| 6,533,804 B2 | 3/2003 | Dobak | 607/105 |
| 6,540,771 B2 | 4/2003 | Dobak | 607/105 |
| 6,544,282 B1 | 4/2003 | Dae | 607/105 |
| 6,551,349 B2 | 4/2003 | Lasheras | 607/105 |
| 6,554,797 B1 | 4/2003 | Worthen | 604/113 |
| 6,558,412 B2 | 5/2003 | Dobak | 607/105 |
| 6,572,538 B2 | 6/2003 | Takase | 600/140 |
| 6,572,638 B1 | 6/2003 | Dae et al. | 607/96 |
| 6,572,640 B1 | 6/2003 | Balding | 607/105 |
| 6,576,001 B2 | 6/2003 | Werneth | 607/96 |
| 6,576,002 B2 | 6/2003 | Dobak | 607/105 |
| 6,581,403 B2 | 6/2003 | Whitebook | 62/434 |
| 6,582,398 B1 | 6/2003 | Worthen | 604/113 |
| 6,582,455 B1 | 6/2003 | Dobak | 607/105 |
| 6,582,457 B2 | 6/2003 | Dae | 607/113 |
| 6,585,692 B1 | 7/2003 | Worthen | 604/113 |
| 6,585,752 B2 | 7/2003 | Dobak | 607/105 |
| 6,589,271 B1 | 7/2003 | Tzeng | 607/113 |
| 6,595,967 B2 | 7/2003 | Kramer | 604/523 |
| 6,599,312 B2 | 7/2003 | Dobak | 607/105 |
| 6,602,243 B2 | 8/2003 | Noda | 604/544 |
| 6,602,276 B2 | 8/2003 | Dobak | 607/105 |
| 6,607,517 B1 | 8/2003 | Dae | 604/31 |
| 6,610,083 B2 | 8/2003 | Keller | 607/105 |
| 6,620,130 B1 | 9/2003 | Ginsburg | 604/113 |
| 6,620,131 B2 | 9/2003 | Pham | 604/113 |
| 6,620,188 B1 | 9/2003 | Ginsburg | 607/106 |
| 6,620,189 B1 | 9/2003 | MacHold | 607/106 |
| 6,623,516 B2 | 9/2003 | Saab | 607/105 |
| 6,635,076 B1 | 10/2003 | Ginsburg | 607/106 |
| 6,641,602 B2 | 11/2003 | Balding | 607/105 |
| 6,641,603 B2 | 11/2003 | Walker | 607/105 |
| 6,645,234 B2 | 11/2003 | Evans | 607/113 |
| 6,648,906 B2 | 11/2003 | Lasheras | 607/105 |
| 6,648,908 B2 | 11/2003 | Dobak | 607/105 |
| 6,652,565 B1 | 11/2003 | Shimada | 607/113 |
| 6,656,209 B1 | 12/2003 | Ginsburg | 607/106 |
| 6,660,028 B2 | 12/2003 | Magers | 607/105 |
| 6,673,098 B1 | 1/2004 | MacHold | 607/106 |
| 6,676,688 B2 | 1/2004 | Dobak | 607/105 |
| 6,676,689 B2 | 1/2004 | Dobak | 607/105 |
| 6,676,690 B2 | 1/2004 | Werneth | 607/105 |
| 6,679,906 B2 | 1/2004 | Hammack | 607/105 |
| 6,679,907 B2 | 1/2004 | Dobak | 607/105 |
| 6,682,551 B1 | 1/2004 | Worthen | 607/105 |
| 6,685,732 B2 | 2/2004 | Kramer | 607/106 |
| 6,685,733 B1 | 2/2004 | Dae | 607/105 |
| 6,692,488 B2 | 2/2004 | Dobak | 606/21 |
| 6,692,519 B1 | 2/2004 | Hayes | 607/105 |
| 6,695,873 B2 | 2/2004 | Dobak | 607/105 |
| 6,695,874 B2 | 2/2004 | MacHold | 607/106 |
| 6,699,268 B2 | 3/2004 | Kordis | 607/113 |
| 6,702,783 B1 | 3/2004 | Dae | 604/113 |
| 6,702,839 B1 | 3/2004 | Dae | 607/96 |
| 6,702,840 B2 | 3/2004 | Keller | 607/105 |
| 6,702,841 B2 | 3/2004 | Nest | 607/105 |
| 6,702,842 B2 | 3/2004 | Dobak | 607/105 |
| 6,706,060 B2 | 3/2004 | Tzeng | 607/105 |
| 6,709,448 B2 | 3/2004 | Walker | 607/105 |
| 6,716,188 B2 | 4/2004 | Noda | 604/6.13 |
| 6,716,236 B1 | 4/2004 | Tzeng | 607/113 |
| 6,719,723 B2 | 4/2004 | Werneth | 604/113 |
| 6,719,724 B1 | 4/2004 | Walker | 604/113 |
| 6,719,779 B2 | 4/2004 | Daoud | 607/105 |
| 6,726,653 B2 | 4/2004 | Noda | 604/113 |
| 6,726,708 B2 | 4/2004 | Lasheras | 607/105 |
| 6,726,710 B2 | 4/2004 | Worthen | 607/105 |
| 6,733,517 B1 | 5/2004 | Collins | 607/105 |
| 6,740,109 B2 | 5/2004 | Dobak | 607/105 |
| 6,749,585 B2 | 6/2004 | Aliberto | 604/113 |
| 6,749,625 B2 | 6/2004 | Pompa | 607/105 |
| 6,752,786 B2 | 6/2004 | Callister | 604/113 |
| 6,755,026 B2 * | 6/2004 | Wallach | 62/3.7 |
| 6,755,850 B2 | 6/2004 | Dobak | 607/104 |
| 6,755,851 B2 | 6/2004 | Noda | 607/113 |
| 2001/0007951 A1 | 7/2001 | Dobak | 607/106 |
| 2001/0016764 A1 | 8/2001 | Dobak, III | 607/105 |
| 2001/0041923 A1 | 11/2001 | Dobak | 607/105 |
| 2002/0007203 A1 | 1/2002 | Gilmartin | 607/105 |
| 2002/0016621 A1 | 2/2002 | Werneth | 607/96 |
| 2002/0068964 A1 | 6/2002 | Dobak | 607/113 |
| 2002/0077680 A1 | 6/2002 | Noda | 600/549 |
| 2002/0091429 A1 | 7/2002 | Dobak | 607/105 |
| 2002/0111616 A1 | 8/2002 | Dea | 606/27 |
| 2002/0151946 A1 | 10/2002 | Dobak, III | 607/105 |
| 2002/0177804 A1 | 11/2002 | Saab | 607/105 |
| 2002/0183692 A1 | 12/2002 | Callister | 604/113 |
| 2002/0193738 A1 | 12/2002 | Adzich | 604/113 |
| 2002/0193853 A1 | 12/2002 | Worthen | 607/3 |
| 2002/0193854 A1 | 12/2002 | Dobak | 607/105 |
| 2003/0078641 A1 | 4/2003 | Dobak | 607/105 |
| 2003/0114835 A1 | 6/2003 | Noda | 604/544 |
| 2003/0144714 A1 | 7/2003 | Dobak | 607/104 |
| 2003/0187489 A1 | 10/2003 | Dobak | 607/105 |
| 2003/0195465 A1 | 10/2003 | Worthen | 604/113 |

| | | | | | | |
|---|---|---|---|---|---|---|
| 2003/0195466 A1 | 10/2003 | Pham | 604/113 | 2004/0102825 A1 | 5/2004 | Daoud |
| 2003/0195597 A1 | 10/2003 | Keller | 607/105 | 2004/0102826 A1 | 5/2004 | Lasheras |
| 2003/0216799 A1 | 11/2003 | Worthen | 606/27 | 2004/0102827 A1 | 5/2004 | Werneth |
| 2003/0225336 A1 | 12/2003 | Callister | 600/505 | 2004/0106969 A1 | 6/2004 | Dobak |
| 2004/0034399 A1 | 2/2004 | Ginsburg | 607/106 | 2004/0111138 A1 | 6/2004 | Bleam ......... 607/105 |
| 2004/0039431 A1 | 2/2004 | Machold | | 2004/0116987 A1 | 6/2004 | Magers |
| 2004/0044388 A1 | 3/2004 | Pham | 607/105 | 2004/0116988 A1 | 6/2004 | Hammack |
| 2004/0050154 A1 | 3/2004 | Machold | | 2004/0127851 A1 | 7/2004 | Noda ......... 604/503 |
| 2004/0054325 A1 | 3/2004 | Ginsburg | 604/113 | 2005/0028551 A1* | 2/2005 | Noda et al. ......... 62/434 |
| 2004/0073280 A1 | 4/2004 | Dae | | | | |
| 2004/0087934 A1 | 5/2004 | Dobak | | * cited by examiner | | |

PRIMARY HEAT EXCHANGER FOR PATIENT TEMPERATURE CONTROL

FILED OF THE INVENTION

The present invention relates generally to patient temperature control systems.

BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, it might be desirable to rewarm a hypothermic patient.

As recognized by the present invention, the above-mentioned advantages in regulating temperature can be realized by cooling or heating the patient's entire body. Moreover, the present invention understands that since many patients already are intubated with central venous catheters for other clinically approved purposes anyway such as drug delivery and blood monitoring, providing a central venous catheter that can also cool or heat the blood requires no additional surgical procedures for those patients. The following U.S. patents, all of which are incorporated herein by reference, disclose various intravascular catheters/systems/methods: U.S. Pat. Nos. 6,749,625, 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, and U.S. patent application Ser. No. 10/355,776. Less optimally, surface cooling can be used. U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference, disclose such surface cooling systems. In both intravascular catheters and external pad systems, coolant such as a gas or saline is circulated through the heat exchange element.

Regardless of the particular heat exchange element that is engaged with the patient, it is clear that heat must be removed from or added to the coolant that flows through the heat exchange element. The present invention makes the following critical observations. Typically, the coolant from the catheter or pad flows through a heat transfer apparatus which warms or cools the coolant using a secondary fluid. The heat transfer apparatus may include a cartridge or bag or other device through which the coolant flows, and the cartridge or bag or other device may be immersed in a secondary fluid bath, with the secondary fluid in the bath exchanging heat with the coolant. Examples of such systems are set forth in some of the above-referenced patents.

As understood herein, when medical personnel engage the coolant bag or cartridge with the secondary fluid bath, the secondary fluid bath may be exposed, and for this reason, in the event that a single electrical fault exists in the system, it is desirable that the bath be grounded for operator safety. The present invention critically recognizes, however, that once the bath is no longer accessible because the primary coolant bag or cartridge is engaged with it, it is desirable from a patient standpoint that the bath not be grounded, in case any leakage current might flow for various fault-related reasons from the pad or catheter.

SUMMARY OF THE INVENTION

A heat exchange system includes a primary coolant heat transfer element through which primary coolant flows from a primary heat exchange element, such as an intravascular catheter or externally-applied pad. A secondary heat transfer element contains a bath of secondary heat exchange fluid. A switch connects the secondary heat transfer element to ground if the primary coolant heat transfer element is not immersed in the bath. On the other hand, the switch disconnects the secondary heat transfer element from ground if the primary coolant heat transfer element is immersed in the bath.

In non-limiting embodiments the switch can be mounted on the secondary heat transfer element and can be biased to a closed position to ground the secondary heat transfer element if the primary heat transfer element is at a predetermined disengaged position. Also, the switch can be moved by the primary heat transfer element to an open position to unground (electrically float) the secondary heat transfer element. In specific non-limiting embodiments the primary heat transfer element includes a hollow sleeve moving the switch, and the sleeve surrounds a hollow coil through which primary coolant flows, while the secondary heat transfer element can include a jacket and a bath container. The sleeve of the primary heat transfer element may be disposed between the jacket and bath container of the secondary heat transfer element when the primary heat transfer element is fully engaged with the secondary heat transfer element, with the coil being disposed in the container. The container holds a secondary heat exchange fluid. A handle may be provided to support supply and return conduits connected to the coil. Closure elements may be attached to the handle and can cover a top end of the sleeve.

In another aspect, a system for exchanging heat with primary coolant flowing through a patient-engageable heat exchange element includes a secondary heat transfer element and a primary heat transfer element engageable with the secondary heat transfer element. The secondary heat transfer element is not grounded if the primary heat transfer element is fully engaged with the secondary heat transfer element during operation. However, the secondary heat transfer element is grounded if the primary heat transfer element is at a disengaged position relative to the secondary heat transfer element.

In yet another aspect, a method for exchanging heat with a patient includes flowing primary coolant through a primary heat exchange element and a primary heat transfer element in a closed loop. The method also includes thermally engaging the primary heat transfer element with a secondary heat transfer element for transferring heat therebetween. As set forth further below, the method contemplates grounding the secondary heat transfer element when a first relative position exists between the primary heat transfer element and the secondary heat transfer element and ungrounding the secondary heat transfer element when a second relative position exists between the primary heat transfer element and the secondary heat transfer element.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
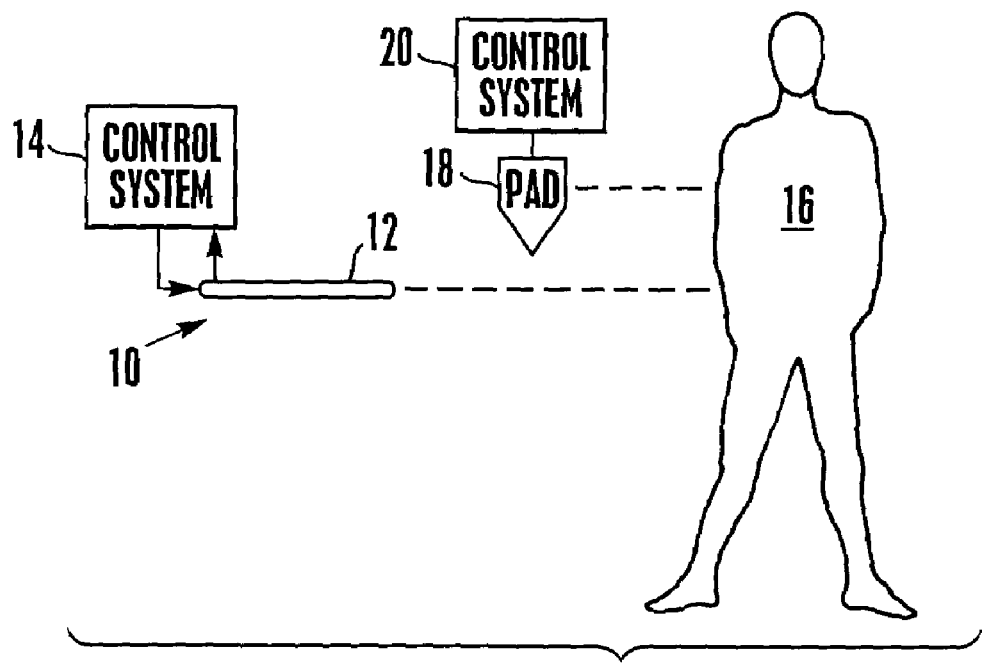
FIG. 1 is a schematic diagram showing two heat exchange modalities.

Referring initially to FIG. 1, a system is shown, generally designated 10, that may include a heat exchange catheter 12 that is in fluid communication with a catheter temperature control system 14 that includes a processor executing logic described in one or more of the patents referenced herein.

In accordance with present principles, the system 10 can be used to induce therapeutic hypothermia in a patient 16 using a catheter in which coolant such as but not limited to saline circulates in a closed loop, such that no coolant enters the body. While certain preferred catheters are disclosed below, it is to be understood that other catheters can be used in accordance with present principles, including, without limitation, any of the catheters disclosed in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by a pad controller 20 in accordance with principles set forth in the external pad patents to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The control systems 14, 20 may be implemented by a single system having one or more processors for executing temperature control algorithms in accordance with the referenced patents.

Figure 2:
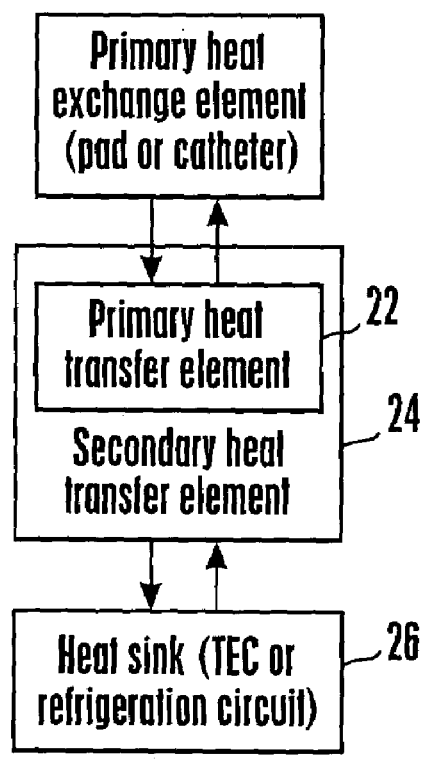
FIG. 2 is a block diagram of a non-limiting implementation of the heat exchange system.

Now referring to FIG. 2, a controller of the present invention may include a primary heat transfer element 22 through which primary coolant flows in a closed loop between the primary heat transfer element 22 and a primary heat exchange element, e.g., the catheter 12 or pad 18 shown in FIG. 1. While the term "coolant" is used of the "primary" fluid, such as saline, that flows through the catheter or pad, it is to be understood that the coolant may be warmer than the patient to heat the patient or colder than the patient to cool the patient. In non-limiting embodiments the primary heat transfer element may be implemented any number of ways. For example, the primary heat transfer element 22 may be a bag or cartridge or, as shown below in the non-limiting embodiment of FIG. 3, it may include a coil through which coolant flows.

In any case, the primary heat transfer element 22 is placed by a medical caregiver in thermal contact with a secondary heat transfer element 24. In one embodiment, the secondary heat transfer element 24 may include a secondary heat exchange fluid (e.g., water or glycol) bath in which the primary heat transfer element 22 is immersed. The temperature of the secondary heat exchange fluid in the secondary heat transfer element 24 (and, thus, the temperature of the coolant in turn) is established by appropriately establishing the operation of a heat sink 26, with the secondary heat exchange fluid circulating in a closed loop or otherwise being in thermal contact with the heat sink 26. In non-limiting embodiments the heat sink 26 may be established by thermo-electric cooler (TEC) apparatus, or a refrigeration circuit, or other suitable heat exchange engine.

Figure 3:
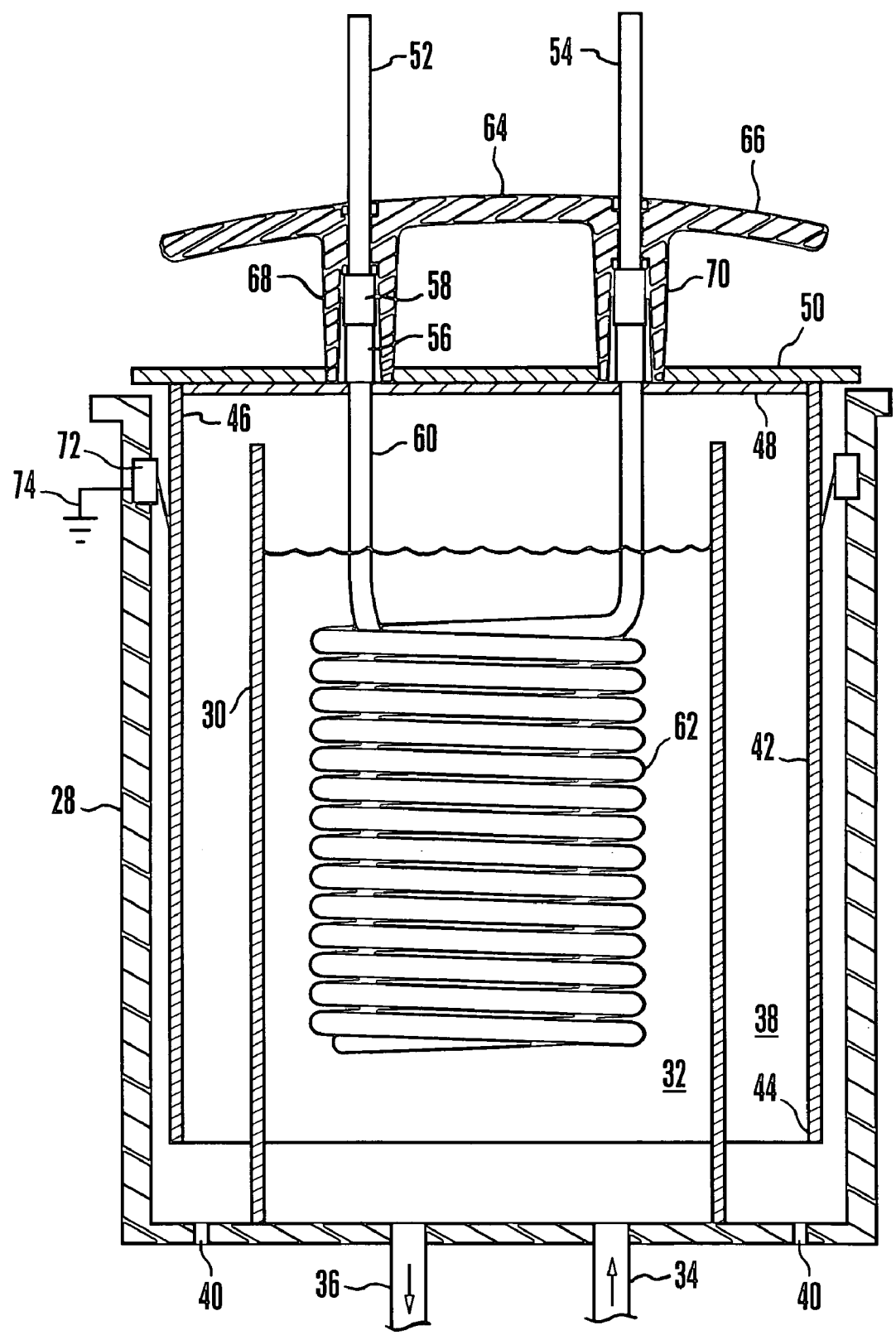
FIG. 3 is a partial cross-sectional view of a non-limiting illustration of the primary-to-secondary heat transfer structure according to the present invention.

Now referring to FIG. 3, non-limiting examples of the primary heat transfer element 22 and secondary heat transfer element 24 can be seen. Starting with the secondary heat transfer element 24, an outer jacket 28 encloses an inner bath container 30, and the inner bath container 30 can hold a secondary heat exchange fluid 32 such as glycol. Secondary heat exchange fluid supply and return ports 34, 36 can be formed in the bath container 30 for circulating secondary heat exchange fluid 32 through the container 30. In the non-limiting embodiment shown, the bath container 32 is radially spaced from the outer jacket 28 to establish an annular empty drainage ring 38 therebetween (i.e., annular when the jacket 28 and container 30 are both cylindrical, as they can be in non-limiting exemplary embodiments). One or more drain connectors 40 can be formed in the bottom of the secondary heat transfer element 24 as shown, to drain any secondary heat exchange fluid 32 that might leak out of the bath container 30.

Turning to a non-limiting example of the primary heat transfer element 22, a hollow sleeve 42 that has opposed open ends and that may be cylindrical is configured as shown for advancement between the outer jacket 28 and bath container 30 of the secondary heat transfer element 24. The walls of the sleeve 42 are spaced from both the outer jacket 28 and container 30 and may be closer to the jacket 28 as shown for engaging the below-described switch that may be mounted thereon, although the switch may be mounted on the bath container 30 and, hence, the sleeve 42 may be configured to be closer to the container 30 than to the jacket 28.

In any case, in the fully engaged position shown, the open bottom end 44 of the sleeve 42 is spaced as shown from the bottom of the secondary heat transfer element 24. The top end 46 of the sleeve 42, on the other hand, is covered with a closure that includes a lower element 48 which fits snugly within the wall of the sleeve 42 and on top of the lower element 48, an upper element 50 rests on the top edge of the sleeve 42 as shown and may be fused thereto by means well known in the art, e.g., gluing, brazing, soldering, rf sealing, etc. The elements 48, 50 may contact each other and may be disk-shaped, so that the top of the sleeve 42 is completely blocked, with the following exception. Primary coolant inlet and outlet conduits 52, 54 extend through the elements 48, 50 of the closure, it being understood that the conduits 52, 54 are connected to respective tubes, such as IV tubes, that lead to the catheter or pad.

In the non-limiting embodiment shown, each conduit 52, 54 includes a respective hollow metal fitting 56 that extends through the upper element 50 of the closure and a respective hollow plastic fitting 58 that is engaged with the metal fitting 56 to connect the metal fitting 56 with the upper tubular portion of the conduit, which upper tubular portion can be plastic. Respective metal tubes 60 are engaged with the metal fittings 56 and depend downwarldly through the lower closure element 48 into the sleeve 42, where they meet opposed ends of a metal or high thermoplastic coil 62.

A plastic handle 64 with opposed gripping ears 66 has hollow legs 68, 70 configured to receive the conduits 52, 54, with the conduits 52, 54 extending completely through the handle 64. Each leg 68, 70 rests on the top of the lower element 48 of the closure as shown and is fused to the upper and/or lower closure element 50, 48. Accordingly, the primary heat transfer element 22 including the coil 62, sleeve 42, closure elements 48, 50, and handle 64 are supplied to the end user as a sealed unitary structure. It may now be appreciated that owing to the use of plastic fittings 58 to engage metal fittings 56, and to the use of a plastic handle 64 and plastic upper portions of the conduits 52, 54, electrical isolation is achieved between the catheter or pad and secondary heat transfer element 24 at least when no primary coolant is present in the primary heat transfer element 22.

Attention is now turned to one or more switches 72, each of which is electrically connected to ground (e.g., to the chassis or ground potential of the controller) through a ground line 74. More than one switch 72 may be used for reliability. In any case, the switch 72 may be mounted near the top of the secondary heat transfer element 24 on the inner wall of the jacket 28 as shown, or it may be mounted on the outer wall of the bath container 30, or any location of the secondary heat transfer element as long as it functions to change position as follows. When the primary heat transfer element 22 is withdrawn from the secondary heat transfer element 24 at and beyond the point where the coil 62 clears the secondary heat exchange fluid 32, the switch 72 is biased closed, so that the jacket 30 is grounded. In contrast, when the primary heat transfer element 22 is advanced far enough into the secondary heat transfer element 24 to the point at which the coil 62 contacts the secondary heat exchange fluid 32, including to the fully engaged position shown in FIG. 3, the sleeve 42 mechanically deflects the switch 72 to its open position, such that the jacket 30 is not grounded, i.e., is floating electrically.

It is to be understood that the present switch alternatively may be a software switch operated by the processor of the control system 14, 20. For example, an optical or magnetic or other presence sensor may be mounted on, e.g., the secondary heat transfer element 24 to sense when the primary heat transfer element 22 is engaged therewith, with the sensor sending a signal indicating the relative positions of the two elements 22, 24 to the processor. Based on the presence sensor signal, the processor can ground or float the system in accordance with principles discussed below.

More specifically and returning to describing the invention in terms of the non-limiting mechanically-operated switch 72 shown in FIG. 3, when the primary heat transfer element 22 is fully engaged with the secondary heat transfer element in the operational configuration shown in FIG. 3, the switch 72 is open and the system as shown floats electrically. On the other hand, when the primary heat transfer element 22 is removed from the secondary heat transfer element 24, exposing the secondary heat exchange fluid 32, the switch 72 is closed and the jacket 29 (more broadly, the secondary heat transfer element 24) is electrically grounded.

With this disclosure in mind, if a person touches the secondary heat exchange fluid 32 while it is exposed, and a single electrical fault exists, current will be shunted to ground through the switch 72, not through the person. On the other hand, when the primary heat transfer element 22 is engaged with the secondary heat transfer element 24 during operation (preventing human access to the bath in the container 30), if a single electrical fault exists, any leakage current that might otherwise pass through the primary coolant and, thus through the coil and the secondary heat exchange fluid to the secondary heat transfer element 24 cannot do so, since the secondary heat transfer element 24 floats in this condition.

While the particular PRIMARY HEAT EXCHANGER FOR PATIENT TEMPERATURE CONTROL as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". It is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. Absent express definitions herein, claim terms are to be given all ordinary and accustomed meanings that are not irreconcilable with the present specification and file history.

What is claimed is:

1. A heat exchange system, comprising:
    a primary heat transfer element through which primary coolant from a primary heat exchange element flows;
    a secondary heat transfer element containing a bath of secondary heat exchange fluid; and
    at least one switch connecting the secondary heat transfer element to ground substantially when the primary coolant heat transfer element is not immersed in the bath and substantially disconnecting the secondary heat transfer element from ground when the primary coolant heat transfer element is immersed in the bath.

2. The system of claim 1, wherein the primary heat exchange element includes an intravascular catheter.

3. The system of claim 1, wherein the primary heat exchange element includes at least one pad applied externally to a patient's skin.

4. The system of claim 1, wherein the switch is mounted on the secondary heat transfer element and is biased to a closed position to ground the secondary heat transfer element when the primary heat transfer element is at a disengaged position, the switch being moved by the primary heat transfer element to an open position to unground the secondary heat transfer element.

5. The system of claim 4, wherein the primary heat transfer element includes a hollow sleeve moving the switch.

6. The system of claim 5, wherein the sleeve surrounds a hollow coil through which primary coolant flows.

7. The system of claim 6, wherein the secondary heat transfer element includes a jacket and a bath container, the sleeve being disposed therebetween when the primary heat transfer element is fully engaged with the secondary heat transfer element, the coil being disposed in the container, the container holding a secondary heat exchange fluid.

8. The system of claim 7, further comprising a handle supporting supply and return conduits connected to the coil and closure elements attached to the handle and covering a top end of the sleeve.

9. A system for exchanging heat with primary coolant flowing through a patient-engageable heat exchange element, comprising:
   a secondary heat transfer element;
   a primary heat transfer element engageable with the secondary heat transfer element, the secondary heat transfer element not being grounded if the primary heat transfer element is fully engaged with the secondary heat transfer element during operation, the secondary heat transfer element being grounded if the primary heat transfer element is at a disengaged position relative to the secondary heat transfer element.

10. The system of claim 9, further comprising at least one switch mounted on the secondary heat transfer element and being biased to a closed position to ground the secondary heat transfer element when the primary heat transfer element is at the disengaged position, the switch being moved by the primary heat transfer element to an open position to unground the secondary heat transfer element.

11. The system of claim 10, wherein the primary heat transfer element includes a hollow sleeve moving the switch.

12. The system of claim 11, wherein the sleeve surrounds a hollow coil through which primary coolant flows.

13. The system of claim 12, wherein the secondary heat transfer element includes a jacket and a bath container, the sleeve being disposed therebetween when the primary heat transfer element is fully engaged with the secondary heat transfer element, the coil being disposed in the container, the container holding a secondary heat exchange fluid.

14. The system of claim 13, further comprising a handle supporting supply and return conduits connected to the coil and closure elements attached to the handle and covering a top end of the sleeve.

15. A method for exchanging heat with a patient, comprising:
   flowing primary coolant through a primary heat exchange element and a primary heat transfer element in a closed loop;
   thermally engaging the primary heat transfer element with a secondary heat transfer element for transferring heat therebetween;
   grounding the secondary heat transfer element when a first relative position exists between the primary heat transfer element and the secondary heat transfer element; and
   ungrounding the secondary heat transfer element when a second relative position exists between the primary heat transfer element and the secondary heat transfer element.

16. The method of claim 15, wherein the acts of grounding and ungrounding are accomplished using a switch.

17. The method of claim 16, wherein the switch is mechanically moved from a first electrical position to a second electrical position by the primary heat transfer element.

* * * * *